United States Patent [19]

Kelleher et al.

[11] Patent Number: 5,461,063
[45] Date of Patent: Oct. 24, 1995

[54] AZABICYCLIC COMPOUNDS

[75] Inventors: Fintan Kelleher, Bishops Stortford; Richard T. Lewis, Harlow, both of England

[73] Assignee: Merck Sharp & Dohme Limited, Hoddesdon, England

[21] Appl. No.: 102,359

[22] Filed: Aug. 5, 1993

[30] Foreign Application Priority Data

Aug. 10, 1992 [GB] United Kingdom ............... 9216911

[51] Int. Cl.$^6$ ............... A61K 31/47; C07D 215/20; C07D 215/36
[52] U.S. Cl. ............... 514/312; 540/593; 546/141; 546/153; 546/154; 546/156; 548/484; 548/488
[58] Field of Search ............... 546/153, 154, 546/156, 141; 514/312, 309

[56] References Cited

FOREIGN PATENT DOCUMENTS

| | | |
|---|---|---|
| 0394989A2 | 10/1990 | European Pat. Off. . |
| 0436334A2 | 7/1991 | European Pat. Off. . |
| 0533280A1 | 3/1993 | European Pat. Off. . |
| WO90/05729 | 5/1990 | WIPO . |
| WO91/18899 | 12/1991 | WIPO . |
| WO92/06079 | 4/1992 | WIPO . |
| WO92/12151 | 7/1992 | WIPO . |

OTHER PUBLICATIONS

"Tachykinin receptors and . . . antagonists" by C. A. Maggi et al., J. Auton. Pharmacol. (1993) vol. 13, pp. 23–93.
Aldrich Chemical Company Ltd. Catalog, 1990, pp. 532 and 1038 (England).
*Cecil Textbook of Medicine*, 19th edition (1992), Wyngaarden, M.D. editor, pp. 2075–2079.

*Primary Examiner*—Philip I. Datlow
*Attorney, Agent, or Firm*—Robert J. North; Melvin Winokur

[57] ABSTRACT

Compounds of formula (I), and salts and prodrugs thereof:

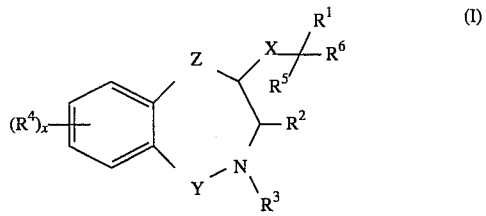

wherein

X represents O or S;
Y represents $(CH_2)_m$, where m is 0 or 1;
Z represents $(CH_2)_n$, where n is 0 or 1;
$R^1$ represents optionally substituted phenyl;
$R^2$ is phenyl, naphthyl, indazolyl, thienyl, furyl, pyridyl, thiazolyl, tetrazolyl, quinolyl, benzhydryl or benzyl;
$R^3$ is H $COR^a$, $CO_2R^a$, $C(COOR)_2$, $C(CONR^aR^b)_2$, $COCONR^aR^b$, $COCO_2R^a$, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, $CON$-$Hphenyl(C_{1-4}$ alkyl), $COCO_2R^a$, $C(=NR^a)NR^bNR^cCO_2R^d$, $CONHNR^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b$-$)NR^cR^d$, $CONR^{13}SO_2R^a$, $SO_2R^{13}COR^a$, $COR^q$, $CON$-$R^a$heteroaryl, and optionally substituted phenyl or $C_{1-6}$alkyl, optionally substituted by oxo, substituted by an optionally substituted aromatic heterocycle;
Each $R^4$ is halo, $C_{1-6}$alkyl, $C_{1-6}$alkoxy or trifluoromethyl;
$R^5$ and $R^6$ are H or $C_{1-6}$alkyl;
$R^a$, $R^b$, $R^c$ and $R^d$ are H $C_{1-6}$alkyl phenyl or trifluoromethyl;
$R^{12}$ represents $OR^a$, $CONR^aR^b$ or heteroaryl;
$R^{13}$ represents H or $C_{1-6}$alkyl;
$R^q$ represents a group

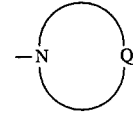

where Q represents the residue of a non-aromatic azacyclic or azabicyclic ring system; and x is 0, 1, 2 or 3; are tachykinin antagonists useful in therapy.

12 Claims, No Drawings

AZABICYCLIC COMPOUNDS

This invention relates to a class of azabicyclic compounds, which are useful as tachykinin antagonists. More particularly, the compounds of the invention comprise an azacyclic ring system, having a fused benzene ring, substituted by an arylmethyloxy or arylmethylthio moiety.

The tachykinins are a group of naturally-occurring peptides found widely distributed throughout mammalian tissues, both within the central nervous system and in the peripheral nervous and circulatory systems. The three known mammalian tachykinins are: substance P, neurokinin A and neurokinin B:

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361-7], immunoregulation [Lotz et al Science (1988) 241 1218-21 and Kimball et al, J. Immunol. (1988) 141 (10) 3564-9], and as anticonvulsants [Garant et al., Brain Research (1986) 382 372-8]. Tachykinin antagonists may also be useful in the treatment of small cell carcinomas, in particular small cell lung cancer (SCLC) [Langdon et al., Cancer Research (1992) 52, 4554-7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

WO-A-90/05729, WO-A-91/18899 and WO-A-92/12151 disclose 3-[cyclic]methylamino-2-[(α-substituted)arylmethyl] quinuclidine compounds which are stated to be useful as substance P antagonists. EP-A-0 436 334 discloses 3-aminopiperidine derivatives as substance P antagonists, and WO-92/06079 discloses related fused bicyclic compounds, also as substance P antagonists. There is no disclosure of azacycles having a fused benzene ring.

The present invention provides a compound of formula (I), or a salt or prodrug thereof:

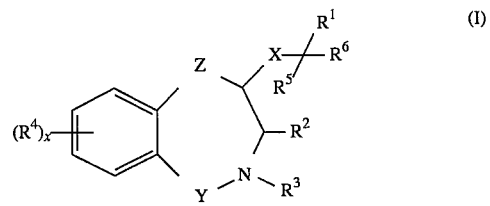

wherein

X represents O or S;

Y represents $(CH_2)_m$, where m is 0 or 1;

Z represents $(CH_2)_n$, where n is 0 or 1;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl —$OR^a$, $SR^a$, $SOR^a$, $SOR^a$, —$NR^aR^b$, —$NR^aCOR^b$, —$NR^aCO_2R^b$, —$CO_2R^a$ and —$CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^3$ represents H, $COR^a$, $COR^a$, $CO_2R^a$, $C(COOR^a)_2$, $C(CONR^aR^b)_2$, $COCONR^aR^b$, $COCO_2R^a$, $C_{1-6}$alkyl optionally substituted by a group selected from ($CO_2R^a$, CON$R^aR^b$, hydroxy, cyano, $COR^a$, $NR^aR^b$, $C(NOH)NR^aR^b$, CONHphenyl($C_{1-4}$alkyl), $COCO_2R^a$, $C(=NR^a)NR^bNR^cCO_2R^d$, CONHN$R^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b)NR^cR^d$, $CONR^{13}SO_2R^a$, $SO_2R^{13}COR^a$, $COR^q$, $CONR^a$heteroaryl, and phenyl optionally substituted by one or more substituents selected from $C_{1-6}$alkyl, $C_{1-6}$alkoxy, halo and trifluoromethyl) or $C_{1-6}$alkyl, optionally substituted by oxo, substituted by an optionally substituted aromatic heterocycle;

Each $R^4$ independently represents halo, $C_{1-6}$alkyl, $C_{1-6}$alkoxy or trifluoromethyl;

$R^5$ and $R^6$ each independently represent H or $C_{1-6}$alkyl;

$R^a$, $R^b$, $R^c$ and $R^d$ each independently represent H, $C_{1-6}$alkyl, phenyl or trifluoromethyl;

$R^{12}$ represents $OR^a$, $CONR^aR^b$ or heteroaryl;

$R^{13}$ represents H or $C_{1-6}$alkyl;

$R^q$ represents a group

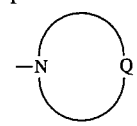

where Q represents the residue of a non-aromatic azacyclic or azabicyclic ring system; and x is 0, 1, 2 or 3.

As used herein, the definition of each expression, when it occurs more than once in any structure, is intended to be independent of its definition elsewhere in the same structure.

The alkyl, alkenyl and alkynyl groups referred to with respect to the formulae herein may represent straight, branched or cyclic groups, or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula I which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

In one subgroup of compounds according to the invention $R^3$ represents H $COR^a$, $CO_2R^a$ or $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, CONHPhenyl($C_{1-4}$alkyl), $COCO_2R^a$, $COCONR^aR^b$ and phenyl optionally substituted by $C_{1-6}$alkyl, $C_{1-6}$alkoxy, halo or trifluoromethyl); and $R^5$ and R6each represent H.

Preferably X represents 0.
Preferably m is 1.
Preferably n is 0.
Preferably $R^1$ represents substituted phenyl.
When $R^1$ is substituted phenyl suitable substituents include nitro, trifluoromethyl, trimethylsilyl, bromo, chloro, fluoro, iodo, cyano, methyl, ethyl, cyclopropyl, vinyl, methoxy, phenoxy, amino and carbonylmethoxy.

Preferably $R^1$ represents phenyl substituted by one or more groups selected from $C_{1-6}$alkyl such as methyl and t-butyl, halo such chloro, bromo and fluoro, $C_{1-6}$alkoxy such as methoxy and trifluoromethyl.

Preferably $R^1$ represents disubstituted phenyl, in particular 3,5-disubstituted phenyl wherein the substituents are selected from $C_{1-6}$alkyl, $C_{1-6}$alkoxy, halo and trifluoromethyl. More preferably $R^1$ represents 3,5-bis(trifluoromethyl)phenyl.

Suitable values for the group $R^2$ include aryl such as unsubstituted or substituted phenyl, 5-membered heteroaryl such as thienyl, 6-membered heteroaryl such as pyridyl, and benzhydryl. When $R^2$ represents substituted phenyl, suitable substituents include halo and trifluoromethyl.

Preferably $R^2$ represents unsubstituted benzhydryl, unsubstituted or substituted phenyl, thienyl, or pyridyl, more preferably unsubstituted benzhydryl, unsubstituted phenyl or phenyl substituted by halo, especially unsubstituted phenyl.

Suitable values for $R^3$ include H, $C_{1-6}$alkyl, such as methyl, and $CO_2R^a$, such as $CO_2(C_{1-6}$alkyl).

Suitable values for $R^4$ include $C_{1-6}$alkyl, such as methyl, $C_{1-6}$alkoxy, such as methoxy, halo, such as chloro and trifluoromethyl.

Preferably x is 0.
Preferably $R^5$ and $R^6$ independently represent H or methyl.

A particular sub-class of compounds according to the invention is represented by compounds of formula (Ia), and salts and prodrugs thereof:

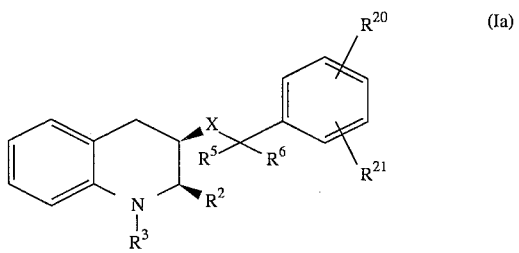

wherein $R^2$, $R^3$, $R^5$, $R^6$ and X are as defined for formula (I);
$R^{20}$ and $R^{21}$ independently represent H $C_{1-6}$alkyl, $C_{2-6}$alkenyl, $C_{2-6}$alkynyl, halo, cyano, nitro, trifluoromethyl trimethylsilyl, $OR^a$, $SR^a$ $SOR^a$, $SO_2R^a$, $NR^aR^b$, $NR^aCOR^b$, $NR^aCO_2R^b$, $COR^a$ or $CONR^aR^b$, where $R^a$ and $R^b$ are as previously defined.

Particular values of $R^{20}$ and $R^{21}$ include methyl, t-butyl, methoxy, chloro, fluoro, bromo and trifluoromethyl. Preferably $R^{20}$ and $R^{21}$ are both other than H and are located at the 3- and 5-positions of the phenyl ring.

For use in medicine, the salts of the compounds of formula (I) will be non-toxic pharmaceutically acceptable salts. Other salts may, however, be useful in the preparation of the compounds according to the invention (such as the dibenzoyltartrate salts) or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, oxalic acid, fumaric acid, maleic acid, succinic acid, acetic acid, citric acid, tartaric acid, carbonic acid, phosphoric acid or ptoluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and ptoluenesulphonic acid salts.

The substance P antagonising activity of compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of the Examples were found to have $IC_{50}$ values less than 500 nM.

The invention also provides pharmaceutical compositions comprising a compound of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I), or a salt or prodrug thereof, for use in therapy.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention may be prepared by a process which comprises reacting a compound of formula (III) with a compound of formula (IV):

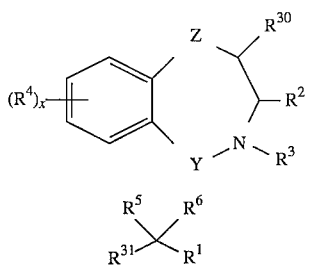

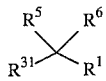

wherein Q, $R^1$, $R^2$, $R^4$, $R^5$, $R^6$, Y, Z and x are as defined for formula (I) above, $R^3$ is as defined for formula (I) or is a protecting group, and one of $R^{30}$ and $R^{31}$ represents a leaving group and the other of $R^{30}$ and $R^{31}$ represents XH, where X is as defined for formula (I); in the presence of a base.

Suitably, $R^{31}$ represents a leaving group and $R^{30}$ represents XH.

Suitable leaving groups include halo, e.g. chloro, bromo or iodo, or sulphonate derivatives such as tosylate or mesylate.

The reaction is conveniently carried out in a suitable organic solvent, such as dimethyl formamide. Favoured bases of use in the reaction include alkali metal hydrides, such as sodium hydride.

Compounds of formula (I) may also be prepared from other compounds of formula (I) using suitable interconversion procedures. In particular, compounds of formula (I) wherein $R^3$ is other than H may be prepared from compounds of formula (I) wherein $R^3$ is H by reaction with a suitable acylating agent or optionally substituted alkylating reagent. Suitable reagents and procedures will be readily apparent to those skilled in the art.

The intermediates of formula (III) above wherein $R^{30}$ is SH may be prepared from the corresponding intermediates of formula (III) wherein $R^{30}$ represents OH by treating the latter compound with Lawesson's reagent or phosphorus pentasulphide in a suitable solvent, e.g. pyridine, at ambient or elevated temperatures, suitably at reflux temperature.

The intermediates of formula (III) above wherein $R^{30}$ is OH and n is 1 may be prepared by reduction of a compound of formula (V):

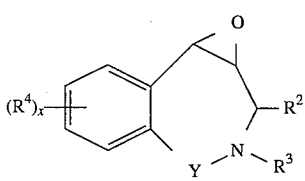

wherein $R^2$, $R^3$, $R^4$, Y and x are as defined for formula (III).

The reaction is suitably effected by means of hydrogenation in the presence of a suitable catalyst, such as a nobel metal catalyst, for example, palladium, which may be supported, for example, on carbon.

Intermediates of formula (III) wherein $R^{30}$ is OH, n is 0, and m is 1 may be prepared by reduction of compounds of formula (VI).

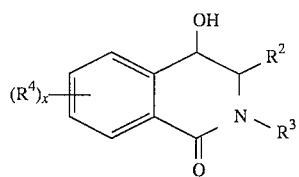

wherein $R^2$, $R^3$, $R^4$ and x are as defined for formula (III).

Suitable reducing agents of use in the reaction include borane.

Intermediates of formula (III) wherein $R^{30}$ is a leaving group may be prepared from compounds of formula (III) wherein $R^{30}$ is OH, for example, by reaction with a thionyl halide, a mesyl halide or a tosyl halide.

Where they are not commercially available, the intermediates of formula (IV) above may be prepared by conventional procedures which will be readily apparent to one skilled in the art.

Compounds of formula (V) may be prepared by epoxidation of the corresponding alkenes of formula (VII)

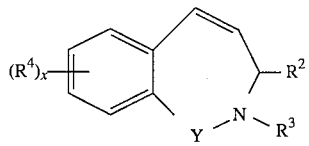

wherein $R^2$, $R^3$, $R^4$, Y and x are as defined for formula (III).

The reaction is conveniently effected using a peracid, for example, m-chloroperbenzoic acid (m-CPBA), and an alkali or alkaline earth metal carbonate, for example, sodium bicarbonate, in a suitable organic solvent, such as a halogenated hydrocarbon, for example, dichloromethane. The epoxidation is preferably effected at low temperature, such as approximately 0° C.

Compounds of formula (VII) wherein $R^3$ is H may be prepared from compounds of formula (VIII)

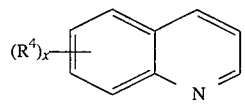

by reaction with a reagent of formula $R^2$-M, where $R^2$ is as defined for formula (I) and M represents an alkali metal, such as lithium.

Compounds of formula (VI) may be prepared by reaction of a compound of formula (IX) with a compound of formula (X)

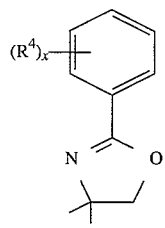

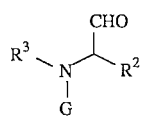

wherein $R^2$, $R^3$, $R^4$ and x are as defined for formula (III) and

G represents a protecting group, in the presence of a base, followed by deprotection.

Suitable bases of use in the reaction include butyl lithiums.

Compounds of formula (VII) wherein $R^3$ is other than H may be prepared from the corresponding compounds wherein $R^3$ is H by conventional procedures.

Compounds of formula (VIII) are commercially available or may be prepared from commerically available starting materials by known processes.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, intermediate alcohols of formula (III), wherein X is oxa, may be resolved into their component enantiomers by standard techniques, such as the formation of diastereomeric esters or amides, followed by chromatographic separation and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following examples illustrate the preparation of compounds according to the invention.

EXAMPLE 1

N-t-Butoxycarbonyl-2-phenyl-3-((3.5bis(trifluoromethyl)phenyl)methyloxy)-2,3,4-trihydroquinoline a) To a solution of quinoline (6 g) in diethyl ether (60 ml) was added a solution of phenyllithium (40 ml, 1.8M) in diethyl ether/cyclohexane) at room temperature. After 2 min the temperature was lowered to −78° C. and a solution of di-t-butyldicarbonate (20.3 g) in diethyl ether (20 ml) was added. The temperature was allowed to rise to room temperature over 3 h and the solution was stirred for a further 16 h. Diethyl ether (100 ml) was added and the solution was washed with water. The organic layer was dried ($Na_2SO_4$) and the solvent removed in vacuo to give N-t-butoxycarbonyl-2-phenyl-2-hydroquinoline. $^1H$ NMR (250MHz, $CDCl_3$)$\delta$6.95–7.6 (9H, m), 6.6 (1H, m), 6.15 (2H, m).

b) m-Chloroperbenzoic add (10.2 g) was added in small portions to a mixture of N-t-butoxycarbonyl-2-phenyl-2-hydroquinoline (Example 1a) and sodium bicarbonate (40 g) in dichloromethane (600 ml) at 0° C. After stirring at room temperature for 5h m-chloroperbenzoic acid (10.sg) was added and the solution was stirred for 16 h. The solution was washed with water and dried ($Na_2SO_4$). Removal of the solvent in vacuo gave an oil which was chromatographed on silica gel in dichloromethane/ethyl acetate/petrol (10:10:80)to give N-t-butoxycarbonyl -2-phenyl-3,4-epoxy-2,3,4-trihydroquinoline (11.2 g). $^1H$ NMR (250MHz, $CDCl_3$)$\delta$7.15–7.42 (9H, m), 6.15 (1H, s), 3.98–4.10 (2H, m), 1.50 (9H, s).

c) N-t-butoxycarbonyl-2-phenyl-3,4-epoxy-2,3,4-trihydroquinoline (11.2 g)was hydrogenated over 10% palladium on charcoal in ethanol (800 ml) at 45 psi for 15 min. The solution was filtered and the solvent was removed in vacuo to give N-t-butoxycarbonyl -2-phenyl-3-hydroxy-2,3,4-trihydroquinoline (7.93 g). $^1H$ NMR (360MHz, $CDCl_3$)$\delta$7.87 (1H, d, J=8.2Hz), 7.02–7.29 (SH, m), 5.19 (1H, d, J=−5.9Hz), 4.01 (1H, m), 2.82 (2H, m), 1.36 (9H, s). m/z ($CI^+$) 326 (M+H).

d) Sodium hydride (0.43g, 60% suspension in oil) was added to a solution of N-t-butoxycarbonyl-2-phenyl-3-hydroxy-2,3,4-trihydroquinoline (3 g) in dimethylformamide (15 ml) at 0° C. After stirring for 30 min 3,5-bis(trifluoromethyl)benzyl bromide (4.24 g) was added and the solution was stirred at room temperature for 3 h. The solution was poured into a saturated ammonium chloride solution and extracted with ethyl acetate. The organic layer was washed with water (x 2) and dried ($Na_2SO_4$). Removal of the solvent in vacuo gave an orange oil which was chromatographed on silica gel in ethyl acetate/petrol (1:9) to give the title compound (4.36 g) after recrystallisation from petrol (60°–80°). $^1H$ NMR (360MHz, $CDCl_3$)$\delta$7.76 (1H, m), 7.69 (2H, s), 7.03–7.29 (SH, m), 5.42 (1H, d, J=5.7Hz), 4.72 (1H, d, J=12.4Hz), 4.57 (1H, d, J=12.4Hz), 3.83 (1H, m), 2.81–2.96 (2H, m), 1.36 (9H, s). m/z ($CI^+$) 552 (M+H). Found: C, 62.69; H, 4.97; N, 2.53. $C_{29}H_{27}NO_3F_6$ requires C, 63.15; H, 4.93; N, 2.54.

EXAMPLE 2

2-Phenyl-3-((3,5-bis(trifluoromethyl)phenyl)methyloxy)-1,2,3,4-tetrahydroquinoline hydrochloride salt The compound of Example 1 (3 g) was dissolved in trifiuoroacetic acid (30 ml) and the resulting solution was stirred for 15 min. The excess trifiuoroacetic acid was removed in vacuo and the residue was dissolved in dichloromethane, washed with (a) 2N sodium hydroxide and (b) water. The organic layer was dried ($Na_2SO_4$). The solvent was removed in vacuo and the residue was dissolved in diethyl ether and excess ethereal-hydrogen chloride was added. The resulting solid was filtered and after recrystallisation from ethyl acetate/methanol gave 2-phenyl -3-((3,5-bis(trifiuoromethyl)phenyl)methyloxy)-1,2,3,4-tetrahydroquinoline hydrochloride salt (2.23 g). $^1H$ NMR (360MHz, $CDCl_3$)$\delta$7.93 (1H, s), 7.75 (1H, s), 7.38 (5H, m), 6.92 (2H, m), 6.51–6.63 (2H, m), 4.80 (1H, d, J=12.9Hz), 4.59 (1H, d, J=12.9Hz), 4.42 (1H, d, 6.2Hz), 3.88–3.93 (1H, m), 2.88 (1H, dd, J=4.9Hz), 2.81 (1H, dd, J=7.5Hz). m/z ($CI^+$) 452 (M+H). Found: C, 57.61; H, 4.13; N, 2.75. $C_{24}H_{20}NOClF_6 \cdot 0.7H_2O$ requires C, 57.59; H, 4.31; N, 2.79.

The following examples illustrate pharmaceutical compositions according to the invention.

EXAMPLE 3A

Tablets Containing 1–25 mg of Compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |

-continued

|  | Amount mg |  |  |
|---|---|---|---|
| Magnesium Stearate | 0.5 | 0.5 | 0.5 |

EXAMPLE 3B

Tablets Containing 26–100 mg of Compound

|  | Amount mg |  |  |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 4

Parenteral Injection

|  | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 5

Topical Formulation

|  | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

We claim:

1. Compounds of formula (Ia), and pharmaceutically acceptable salts and prodrugs thereof:

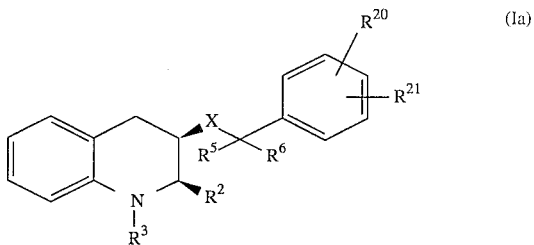

wherein

X represents O or S;

$R^2$ represents aryl selected from phenyl and naphthyl.; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^3$ represents H, $COR^a$, $CO_2R^a$, $CH(COOR^a)_2$, $CH(CONR^aR^b)_2$, $COCONR^aR^b$, $COCO_2R^a$, $C_{1-6}$alkyl optionally substituted by a group selected from: $CO_2R^a$, $CONR^aR^b$, hydroxy, cyano, $COR^a$, $NR^aR^b$, $C(NOH)NR^aR^b$, $CONHphenyl(C_{1-4}alkyl)$, $COCO_2R^a$, $C(=NR^a)NR^bNR^cCO_2R^d$, $CONHNR^aR^b$, $C(S)NR^aR^b$, $CONR^aC_{1-6}$alkylene $R^{12}$, $CONR^{13}C_{2-6}$alkynyl, $CONR^{13}C_{2-6}$ alkenyl, $COCONR^aR^b$, $CONR^aC(NR^b)NR^cR^d$, $CONR^{13}SO_2R^a$, $CORq$, $CONR^a$heteroaryl, wherein said heteroaryl is defined above, and phenyl optionally substituted by one or more substituents selected from $C_{1-6}$alkyl, $C_{1-6}$ alkoxy, halo and trifluoromethyl; or $R^3$ represents $C_{1-6}$alkyl which can be optionally substituted by a substituent selected from the group consisting of: oxo, and substituted or unsubstituted heteroaryl as defined above;

$R^5$ and $R^6$ each independently represent H or $C_{1-6}$alkyl;

$R^a$, $R^b$, $R^c$ and $R^d$ each independently represent H, $C_{1-6}$alkyl, phenyl or trifluoromethyl;

$R^{12}$ represents $OR^a$, $CONR^aR^b$ or heteroaryl as defined above;

$R^{13}$ represents H or $C_{1-6}$alkyl;

Rq represents a N-linked non-aromatic azacyclic or azabicyclic ring system;

$R^{20}$ and $R^{21}$ independently represent H, $C_{1-6}$alkyl, $C_{2-6}$alkenyl, $C_{2-6}$alkynyl, halo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$ or $CONR^aR^b$, where $R^a$ and $R^b$ are defined above.

2. A compound as claimed in claim 1 wherein $R^3$ represents H, $COR^a$, $CO_2R^a$ or $C_{1-6}$alkyl optionally substituted by a group selected from $CO_2R^a$, $CONR^aR^b$, hydroxy, cyano, $COR^a$, $NR^aR^b$, $C(NOH)NR^aR^b$, $CONHphenyl(C_{1-4}alkyl)$, $COCO_2R^a$, $COCONR^aR^b$ and phenyl optionally substituted by $C_{1-6}$alkyl, $C_{1-6}$alkoxy, halo or trifluoromethyl; and $R^5$ and $R^6$ each represent H.

3. A compound as claimed in claim 1 wherein X is O.

4. A compound as claimed in claim 1 wherein $R^2$ represents unsubstituted benzhydryl, unsubstituted phenyl or phenyl substituted by halo.

5. A compound as claimed in claim 1 wherein $R^3$ is H, $C_{1-6}$alkyl or $CO_2R^a$.

6. A compound as claimed in claim 1 wherein $R^5$ and $R^6$ each independently represent H or methyl.

7. A compound as claimed in claim 1 selected from:

N-t-butoxycarbonyl-2-phenyl-3-((3,5-bis (trifluoromethyl)phenyl)methyloxy)-2,3,4trihydroquinoline;

2-phenyl-3-((3,5-bis(trifluoromethyl)phenyl)methyloxy)-1,2,3,4-tetrahydroquinoline; and salts and prodrugs thereof.

8. A pharmaceutical composition comprising a compound as claimed in claim 1 in association with a pharmaceutically acceptable carrier.

9. A method for the treatment or prevention of a physiological disorder associated with an excess of tachykinins, which method comprises administration to a patient in need thereof of a tachykinin-reducing amount of a compound according to claim 1.

10. A method according to claim 9 for the treatment or prevention of pain or inflammation.

11. A method according to claim 9 for the treatment or prevention of migraine.

12. A method according to claim 9 for the treatment or prevention of arthritis.

\* \* \* \* \*